(12) United States Patent
Kim et al.

(10) Patent No.: US 7,022,068 B2
(45) Date of Patent: Apr. 4, 2006

(54) ENDOSCOPE SYSTEM WITH A HOLLOW CYLINDER AND A BELLOWS MOVING MECHANISM

(75) Inventors: ByungKyu Kim, Seoul (KR); YounKoo Jeong, Seoul (KR); Hun-Young Lim, Seoul (KR); Tae-Song Kim, Seoul (KR); Jong-Oh Park, Seoul (KR); Paolo Dario, Livorno (IT)

(73) Assignee: Korea Institute of Science and Technology, Seoul (KR)

( * ) Notice: Subject to any disclaimer, the term of this patent is extended or adjusted under 35 U.S.C. 154(b) by 34 days.

(21) Appl. No.: 10/635,172

(22) Filed: Aug. 6, 2003

(65) Prior Publication Data

US 2004/0030219 A1 Feb. 12, 2004

(30) Foreign Application Priority Data

Aug. 6, 2002 (KR) ..................... 10-2002-0046392

(51) Int. Cl.
*A61B 1/01* (2006.01)
*A61B 1/05* (2006.01)
(52) U.S. Cl. ...................................... 600/115; 600/173
(58) Field of Classification Search ........ 600/114–116, 600/156, 158, 159, 173, 146, 152; 604/95.01, 604/95.03, 95.04, 95.05, 103.03; 73/865.8, 73/866.5; 606/108
See application file for complete search history.

(56) References Cited

U.S. PATENT DOCUMENTS

| | | | | |
|---|---|---|---|---|
| 3,895,637 A | * | 7/1975 | Choy | 604/95.03 |
| 4,676,228 A | * | 6/1987 | Krasner et al. | 600/116 |
| 5,090,259 A | * | 2/1992 | Shishido et al. | 73/866.5 |
| 5,144,848 A | * | 9/1992 | Uenishi et al. | 73/866.5 |
| 5,398,670 A | * | 3/1995 | Ortiz et al. | 600/114 |
| 5,906,591 A | * | 5/1999 | Dario et al. | 604/95.03 |
| 6,007,482 A | * | 12/1999 | Madni et al. | 600/115 |
| 6,517,477 B1 | * | 2/2003 | Wendlandt | 600/114 |
| 6,542,081 B1 | * | 4/2003 | Torch | 340/575 |
| 6,626,824 B1 | * | 9/2003 | Ruegg et al. | 600/104 |
| 6,869,397 B1 | * | 3/2005 | Black et al. | 600/168 |
| 2002/0087525 A1 | * | 7/2002 | Abbott et al. | 707/3 |
| 2003/0065250 A1 | * | 4/2003 | Chiel et al. | 600/115 |
| 2003/0127261 A1 | * | 7/2003 | Borroni-Bird et al. | 180/65.1 |
| 2005/0104802 A1 | * | 5/2005 | Hebert et al. | 345/7 |

* cited by examiner

Primary Examiner—John P. Leubecker
(74) Attorney, Agent, or Firm—Patterson & Sheridan, L.L.P.

(57) ABSTRACT

An endoscope system with a hollow cylinder and bellows moving mechanism is provided. The system includes a cylinder having a head unit mounted by a camera devices, a front fixing unit connected to the head unit which is installed to an outer circumference of the cylinder and fixed to an inner wall of an organ, a rear fixing unit slidably installed at the outer circumference of the cylinder and fixed to the inner wall of the organ, and a moving unit between the front fixing unit and the rear fixing unit for moving the head unit in the organ by an extension and contraction when the front fixing unit or the rear fixing unit fixes the head unit to the inner wall of the organ. The moving unit includes a double bellows and forms a hermetic space with the outer circumference surface of the cylinder.

18 Claims, 7 Drawing Sheets

ENDOSCOPE SYSTEM WITH A HOLLOW CYLINDER AND A BELLOWS MOVING MECHANISM

BACKGROUND OF THE INVENTION

1. Field of the Invention

The present invention relates to an endoscope system

2. Description of the Background Art

An endoscope has been widely used in a medical field in accordance with that fiber optics and a micro camera are developed.

However, in case of a large intestine endoscope, since an organ structure is complicatedly curved with a third dimensional shape and a degree of freedom of a movement of the endoscope is limited, more time and effort have to be spent to obtain a technique by which the endoscope is inserted into the organ. Also, a doctor cannot concentrate on a diagnosis or an operation but consumes much energy to handle the endoscope.

A accurate diagnosis depends not only on a doctor's medical knowledge or an experience but also on a technique to handle the endoscope, which causes low determination rate of a sick part for the endoscope diagnosis which is different according to doctors.

SUMMARY OF THE INVENTION

Therefore, an object of the present invention is to provide an endoscope system having a simple fabrication method and an easy control in which a control unit, a diagnosis tool, and etc. are mounted by constituting a body.

To achieve these and other advantages and in accordance with the purpose of the present invention, as embodied and broadly described herein, there is provided an endoscope system having a body comprising: a head unit having a camera device at one side thereof; a cylinder connected to a tube which is connected to an external device out of a human body; a front fixing unit connected to the head unit, installed to an outer circumference of the cylinder, and thereby fixable to an inner wall of an organ; a rear fixing unit slidably installed at the outer circumference of the cylinder and fixable to the inner wall of the organ; and a moving unit connectedly installed between the front fixing unit and the rear fixing unit for moving the head unit in the organ by an extension and contraction when the front fixing unit or the rear fixing unit fixes the head unit to the inner wall of the organ.

To achieve these and other advantages and in accordance with the purpose of the present invention, as embodied and broadly described herein, there is also provided an endoscope system further comprising: a recognizing unit for recognizing a movement of an observer's pupil; and a control unit for generating a control signal according to the pupil's movement recognized by the recognizing unit, wherein an imaging position of a camera and a steering angle of a body are controlled by a signal of the control unit.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
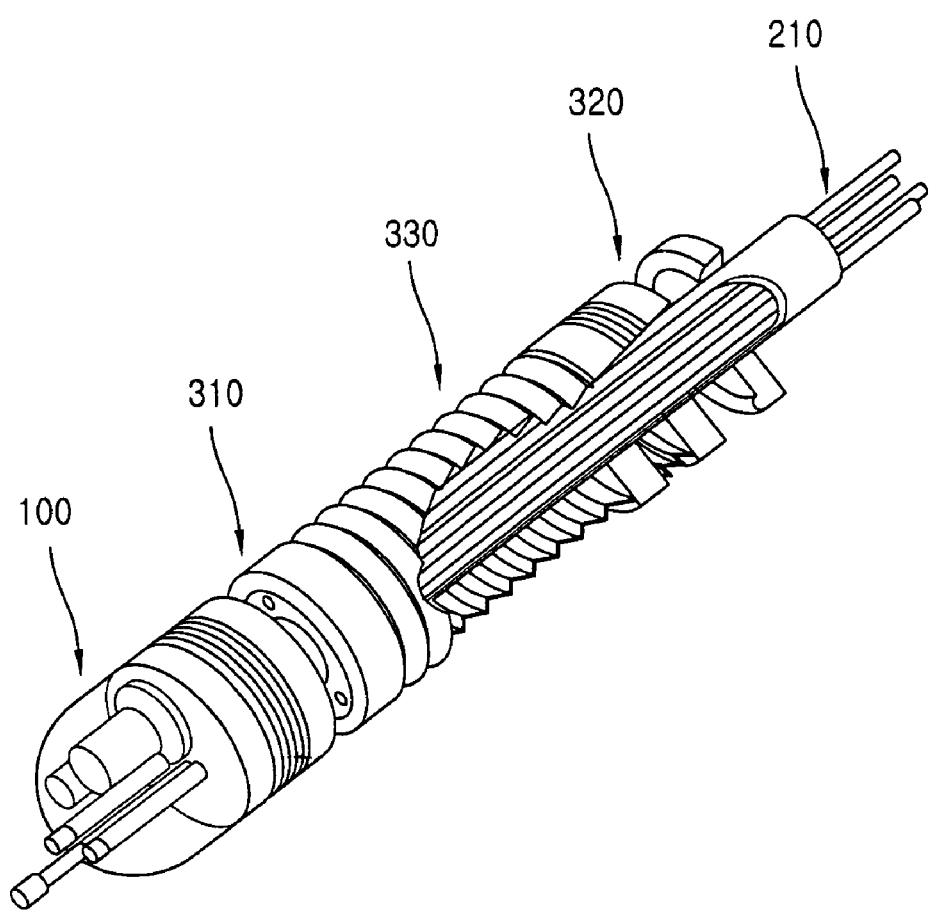
FIG. 1 is a perspective view showing an endoscope system according to one preferred embodiment of the present invention.
Figure 2:
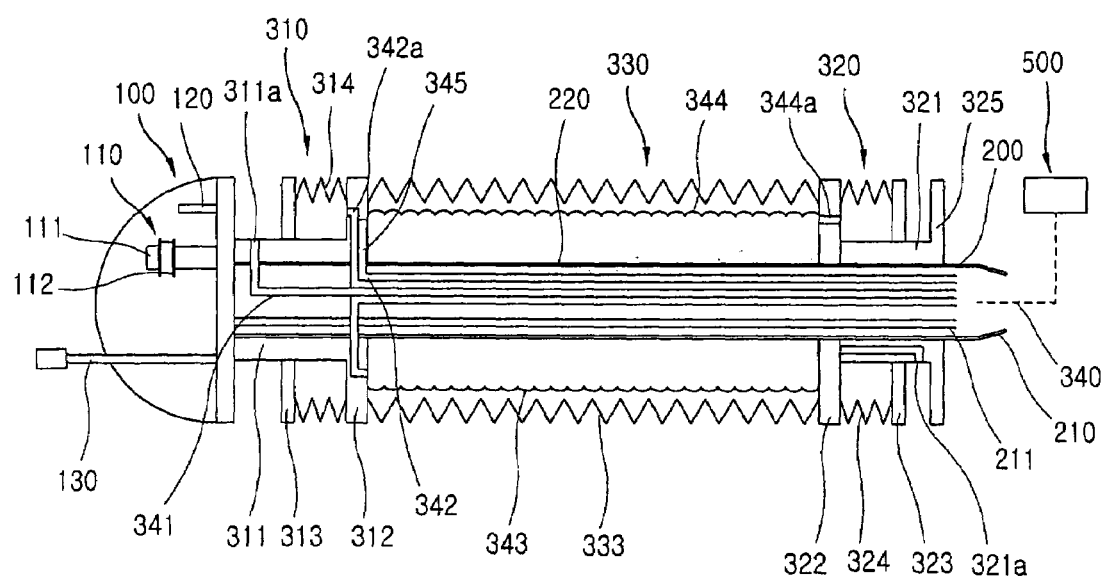
FIG. 2 is a sectional view showing the endoscope system of FIG. 1.

As shown in FIGS. 1 and 2, a body 1 of the endoscope system comprises: a head unit 100 having a camera device 110 at one side thereof; a cylinder 200 connected to a tube 210 which is connected to an external device 500 out of a human body; a front fixing unit 310 connected to the head unit 100, installed to an outer circumference of the cylinder 200, and thereby fixed to an inner wall of an organ; a rear fixing unit 320 slidably installed at the outer circumference 220 of the cylinder 200 and fixed to the inner wall of the organ; and a moving unit 330 connectedly installed between the front fixing unit 310 and the rear fixing unit 320 for moving the head unit 100 in the organ by an extension and contraction when the front fixing unit 310 or the rear fixing unit 320 fixes the head unit 100 to the inner wall of the organ.

Examination objects by the endoscope system of the present invention are an esophagus, a small intestine, a large intestine and etc.

The camera device 110 is for imaging an inner wall of the organ so as to see a stationary image or a motion video for the inner wall of the organ. A camera 111 of the camera device 110 includes a CMOS (complementary metal oxide semiconductor), a CCD (charge coupled device), or an infrared rays camera. Preferably, a focus distance of the camera 111 has to be adjusted automatically. Especially, the focus distance can be automatically adjusted by moving connectedly with the pupil's movement recognized by a recognizing unit 520 which will be explained later.

The camera device 110 is connected to the external device 500 out of the human body by a signal connecting line 211 which passes a hole of the cylinder 200 and the tube 210. Image information obtained by the camera 111 is transmitted to the external device 500 through the signal connecting line 211, thereby being outputted to a monitor 511. Or, a control signal of the external device 500 for controlling the camera device 110 is transmitted to the camera device 110 through the signal connecting line 211. The camera device 110 can exchange the control signal and the image information by using a radio transmittance and reception device (not shown) instead of the signal connecting line 211.

Figure 3:
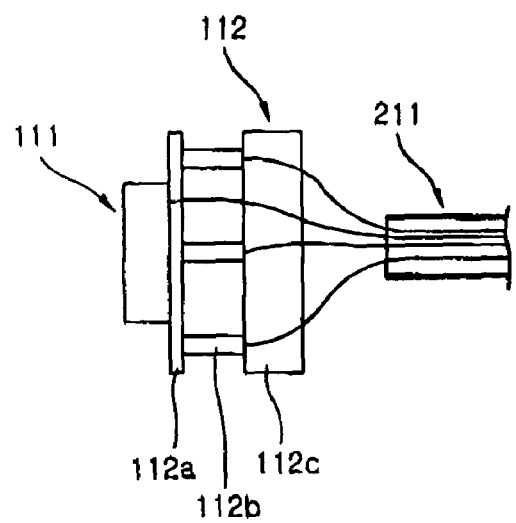
FIG. 3 is a lateral view showing a steering system of the endoscope system according to the present invention.

As shown in FIG. 3, the camera device 110 can further include a steering system 112 for adjusting an imaging direction of the camera 111. The steering system 112 includes an upper plate 112a on which the camera 111 is mounted; a lower plate 112c fixed to the head unit 100; and a plurality of connecting bridges 112b for changing the imaging direction of the camera 111 by connecting the upper plate 112a and the lower plate 112c and having a changed length thereof.

As the connecting bridge 112b, functional polymer of which length is changed by an electric energy or a pneumatic cylinder can be used.

The head unit 100 can include not only the camera device 110 but also an illuminating device 120 for illuminating light at the inner wall of the organ so as to obtain an image by the camera 111, a frequency generating unit for generating an infrared rays light source (not shown) for a virtual biopsy or a constant frequency.

That is, the illuminating device 120 can use a light fiber, and the infrared rays light source for the virtual biopsy can use a multi-wave light source which radiates wave of an infrared rays region.

Also, the head unit 100 may be provided with a various type of diagnosis tool 130 which examines a structure of the inner wall of the organ, eliminates, separates some parts, or injects dye reacting with a cancer cell.

The cylinder 200 is connected with the tube 210 connected with the external device 500 out of the human body. In the cylinder, a pneumatic lines 340 for transmitting pneumatic pressure to the front fixing unit 310, the rear fixing unit 320, and the moving unit 330, the signal connecting line 211, and a tool (not shown) for performing an additional function such as a cure besides a virtual biopsy at the endoscope are mounted.

Also, the cylinder 200 and the tube 210 are made of silicon or polyurethane suitable to the human body. The cylinder 200 is fabricated to be easily curved in a large intestine having many curved parts in order to easily move.

The front fixing unit 310 and the rear fixing unit 320 are fixed to the inner wall of the organ by the control signal of the control unit 510 of the external device 500 so that the endoscope system moves or stops in the organ.

The front fixing unit 310 includes a front fixing cylinder member 311 fitted to an outer side of the cylinder 200 and connected to the head unit 100; a second front fixing frame member 312 extended from a free end of the front fixing cylinder member 311 to an outer side direction of the cylinder 200; a first front fixing frame member 313 fitted to an outer side of the front fixing cylinder member 311 and installed to be slidable with the outer circumference surface thereof; and a front fixing bellows 314 of which both ends are fixed to the first and second front fixing frame members 312 and 313 and extended and contracted by amount of air inside thereof.

A plurality of holes 311a are formed at a side adjacent to the head unit 100 at the outer circumference surface of the front fixing cylinder member 311. The plurality of holes 311a are connected to a first pneumatic line 341 formed therein to suck and exhaust air.

The second front fixing frame member 312 is provided with an air inlet 342a for supplying or exhausting air to the inner portion of the front fixing bellows 314. At this time, the air inlet is connected to a second pneumatic line 342.

The first and second pneumatic lines 341 and 342 are connected to a pneumatic generating device (not shown), and the pneumatic generating device can be additionally installed at the inner portion of the cylinder 200 or can be installed at the outer portion of the human body through the tube 210. Also, the first and second pneumatic lines 341 and 342 can be connectedly installed from the head unit 200 or connected by penetrating the outer side of the cylinder 200.

The rear fixing unit 320 includes a rear fixing cylinder member 321 slidably fitted to an outer side of the cylinder 200 with a predetermined distance with the front fixing member 310; a first rear fixing frame member 322 extended from an end portion of the rear fixing cylinder member 321 of a side adjacent to the front fixing unit 310 to an outer side direction of the cylinder 200; a rear frame member 325 extended from the end portion of the rear fixing cylinder member 321 to the outer side of the cylinder 200; a second rear fixing frame member 323 fitted to an outer side of the rear fixing cylinder member 321 and installed to be slidable with the outer circumference surface thereof; and a rear fixing bellows 324 of which both ends are fixed to the first and second front fixing frame members 322 and 323 and extended and contracted by amount of air inside thereof.

A plurality of holes 321a are formed at a side adjacent to the second rear fixing frame 323 at the outer circumference surface of the rear fixing cylinder member 321. The plurality of holes 321a are connected to a third pneumatic line 343 to suck and exhaust air.

The first rear fixing frame member 322 is provided with an air inlet 344a for supplying or exhausting air to the inner portion of the rear fixing bellows 324. At this time, the air inlet is connected to a fourth pneumatic line 344.

The third and fourth pneumatic lines 343 and 344 are connected to a pneumatic generating device, and the pneumatic generating device can be additionally installed at the inner portion of the cylinder 200 or can be installed at the outer portion of the human body through the tube 210. Also, the third and fourth pneumatic lines 343 and 344 is connectedly installed from the head unit 100 to the front fixing unit 310 and a moving unit 330 which will be later explained.

The moving unit 330 is installed by connecting the front fixing unit 310 and the rear fixing unit 320, and extended or contracted by the control signal of the control unit 510 of the external device 500.

The moving unit 330 has a space at a center thereof where the cylinder 200 is installed, and the construction thereof is various.

That is, as shown in FIG. 2, the moving unit 330 of the endoscope system according to the first preferred embodiment of the present invention is installed with an interval to the outer side direction of the cylinder 200. The moving unit 330 includes the second front frame member 312, the first rear frame member 322, and a first moving bellows 333 forming a hermetic space with the outer circumference surface of the cylinder 200.

The second front frame member 312 is provided with an air exhausting hole 325 for injecting or exhausting air to the hermetic space at the hermetic space side, and the air exhausting hole 321 a is connected to a fifth pneumatic line 345.

The fifth pneumatic line 345 is connected to a pneumatic generating device, and the pneumatic generating device can be additionally installed at the inner portion of the cylinder 200 or can be installed at the outer portion of the human body through the tube 210. Also, the fifth pneumatic lines 345 can be connectedly installed from the head unit 100 or connected by penetrating the outer side of the cylinder 200.

Especially, the third and fourth pneumatic lines 343 and 344 are connected to the first rear frame member 322 through the hermetic space. Also, an inner circumference surface of the rear fixing cylinder member 321 of the rear fixing unit 320 and the outer circumference surface of the cylinder 200 are slidable interactively, and adhered to prevent air leakage from the hermetic space or sealed by using an additional sealing member (not shown).

Herein, a proportional control valve can be used to control a precise pressure of the first and fifth pneumatic lines.

Figure 4:
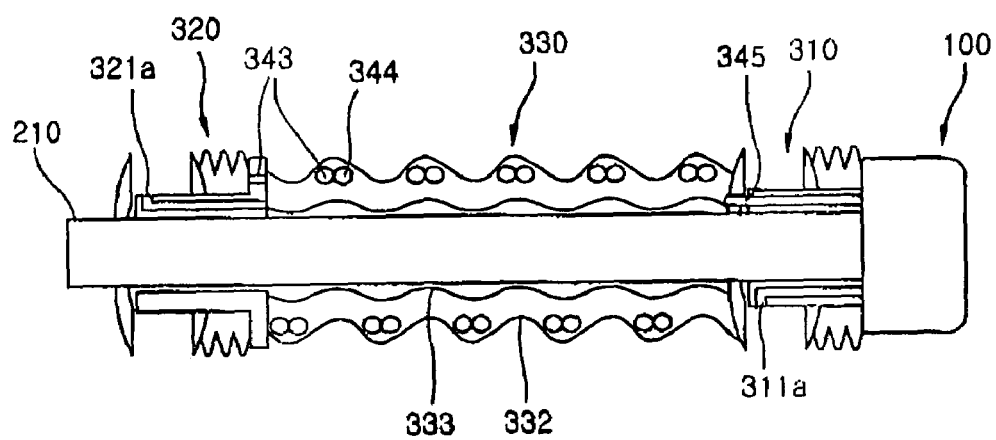
FIG. 4 is a sectional view showing the endoscope system according to a second preferred embodiment of the present invention.

As shown in FIG. 4, the moving unit 330 of the endoscope system according to the second preferred embodiment of the present invention needs not form the hermetic space with the outer circumference surface of the cylinder 200 but has an additional second moving bellows 332 differently from the first preferred embodiment.

That is, a double moving bellows having a sectional surface of a doughnut shape is installed to form the hermetic space. In this case, a sealing for preventing air from being introduced or exhausted to the interval between the rear fixing unit 320 and the cylinder 200 is not required to form the hermetic space.

Figure 5:
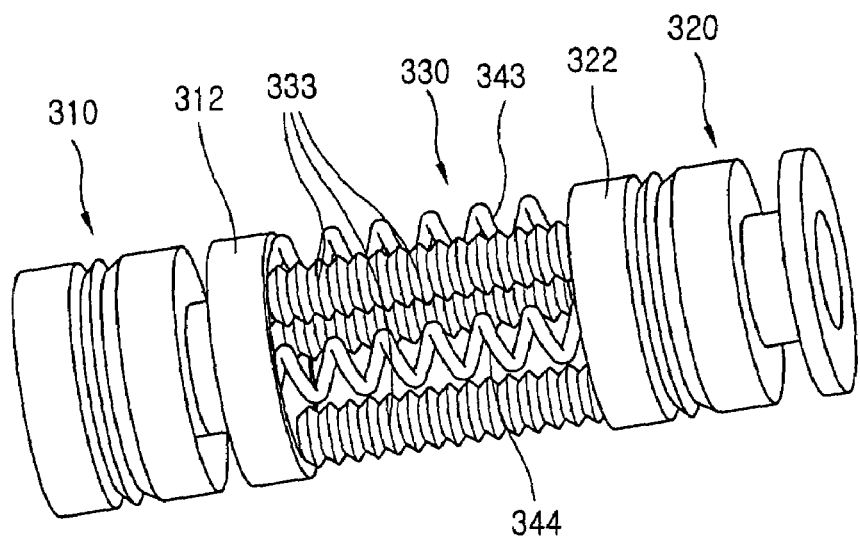
FIG. 5 is a perspective view showing the endoscope system according to a third preferred embodiment of the present invention.

As shown in FIG. 5, in the moving unit 330 of the endoscope system according to the third preferred embodiment of the present invention, a plurality of bellows 333 radially arranged to the outer circumference surface of the cylinder 200 are connectedly installed at the second front fixing frame 313 and the first rear fixing frame 322.

A plurality of air exhausting holes 325 for injecting or exhausting air to the inner portion of the plurality of bellows 333 are respectively formed at the second front bellows 313, and the plurality of air exhausting holes 325 is connected to the fifth pneumatic line 345 like the endoscope system of the first preferred embodiment of the present invention.

At this time, the third and fourth pneumatic lines 343 and 344 are connected to the first rear frame member 312 around the outer circumference surface of the cylinder 200.

Also, the moving unit 330 of the endoscope system according to the third preferred embodiment of the present invention may use functional polymer (not shown) of which a length is extended or contracted by an electricity appliance instead of the plurality of bellows or a linear motor (not shown).

In the meantime, the endoscope system according to the present invention provides the external device 500 including a recognizing unit 520 so that an observer can easily and precisely control the system.

Figure 6:
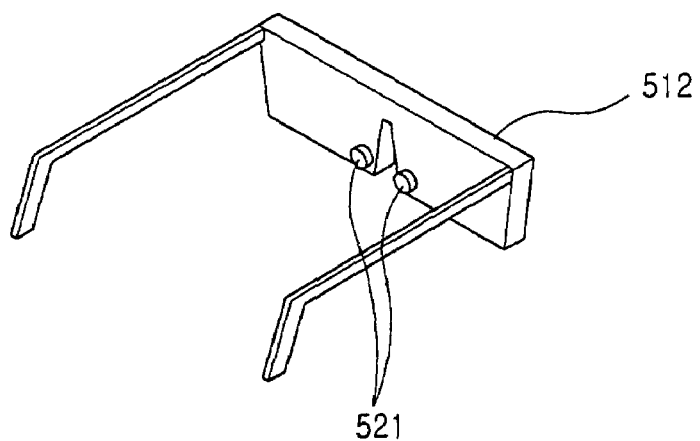
FIG. 6 is a conceptual view showing a recognizing unit of the endoscope system according to the present invention.
Figure 7:
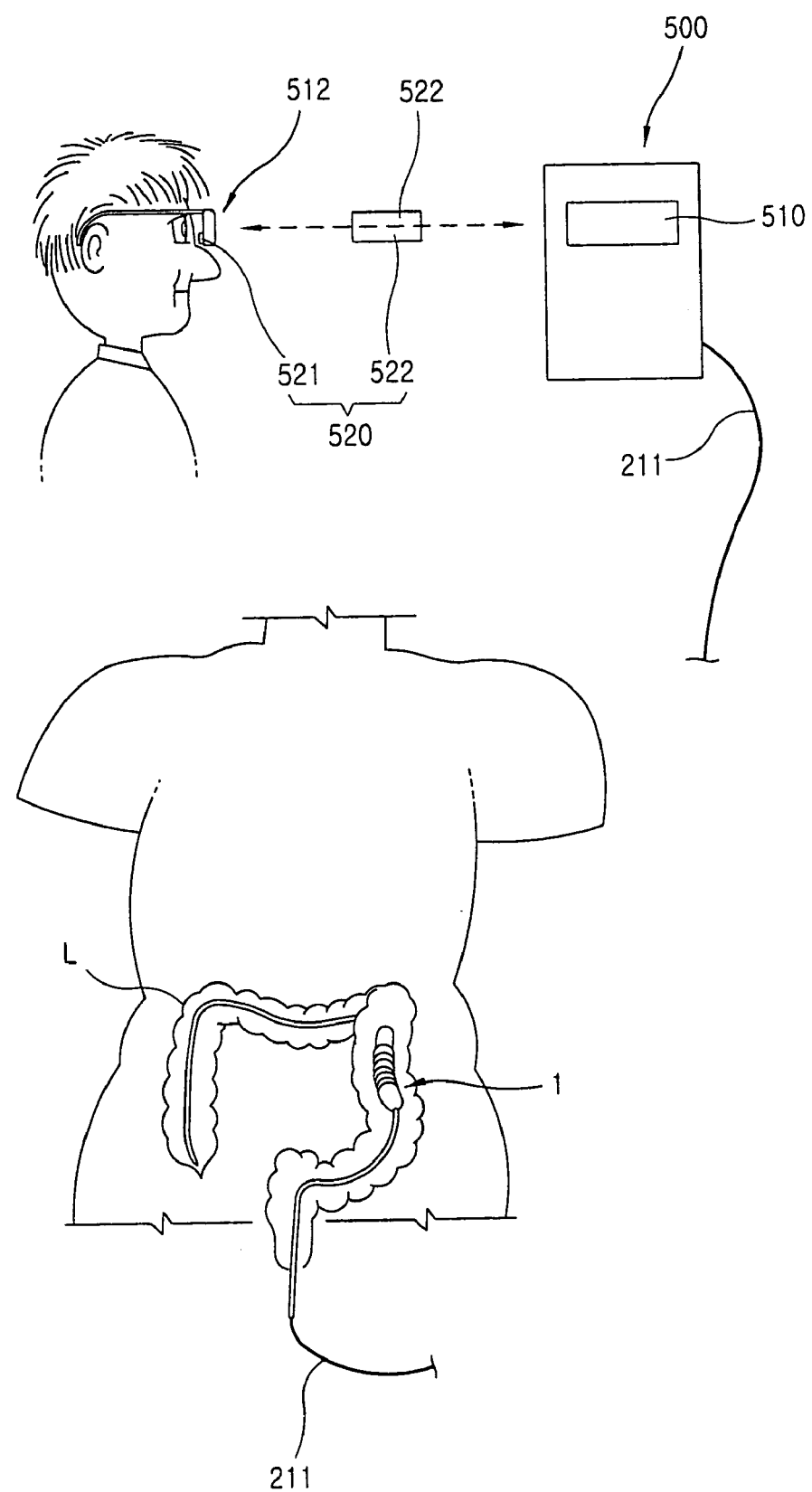
FIG. 7 is a conceptual view of a head mounted display of the endoscope system according to the present invention.

As shown in FIGS. 6 and 7, the recognizing unit 520 recognizes the observer's pupil movement and generates a signal according to the pupil's movement, thereby transmitting to the control unit 510. The control unit 510 generates a control signal to control an imaging location of the camera 111 and a movement of the body 1.

The recognizing unit 520 includes a recognizing camera 521 for imaging the observer's eyes, and an image processing unit 522 for recognizing the pupil's movement from the obtained image. Especially, by recognizing the pupil's reaction, the recognizing unit can control not only the imaging direction of the camera 111 or the movement of the body 1 but also a focus distance of the camera 111 or a brightness of the illuminating device 120.

Also, the recognizing unit 520 may include a detecting device (not shown) for recognizing the pupil's movement by measuring an electromyogram of a muscle around the observer's eyes.

Also, a joystick 531 or a touch screen 532 may be used as a means for controlling an imaging location of the camera 111 or the movement of the body 1.

In the meantime, a monitor 511 or a head mounted display 512 can be generally used as a device for outputting the image information obtained by the camera 111.

Especially, a micro camera as a recognition camera 521 of the recognizing unit 520 can be additionally mounted to the head mounted display 512 so that the observer can control the endoscope system. Also, supplementary monitors 511a can be additionally installed for the third man, that is, a patient or another observer except the observer.

The control unit 510 transmits the control signal to the body 1 by wire or wirelessly.

Figure 8:
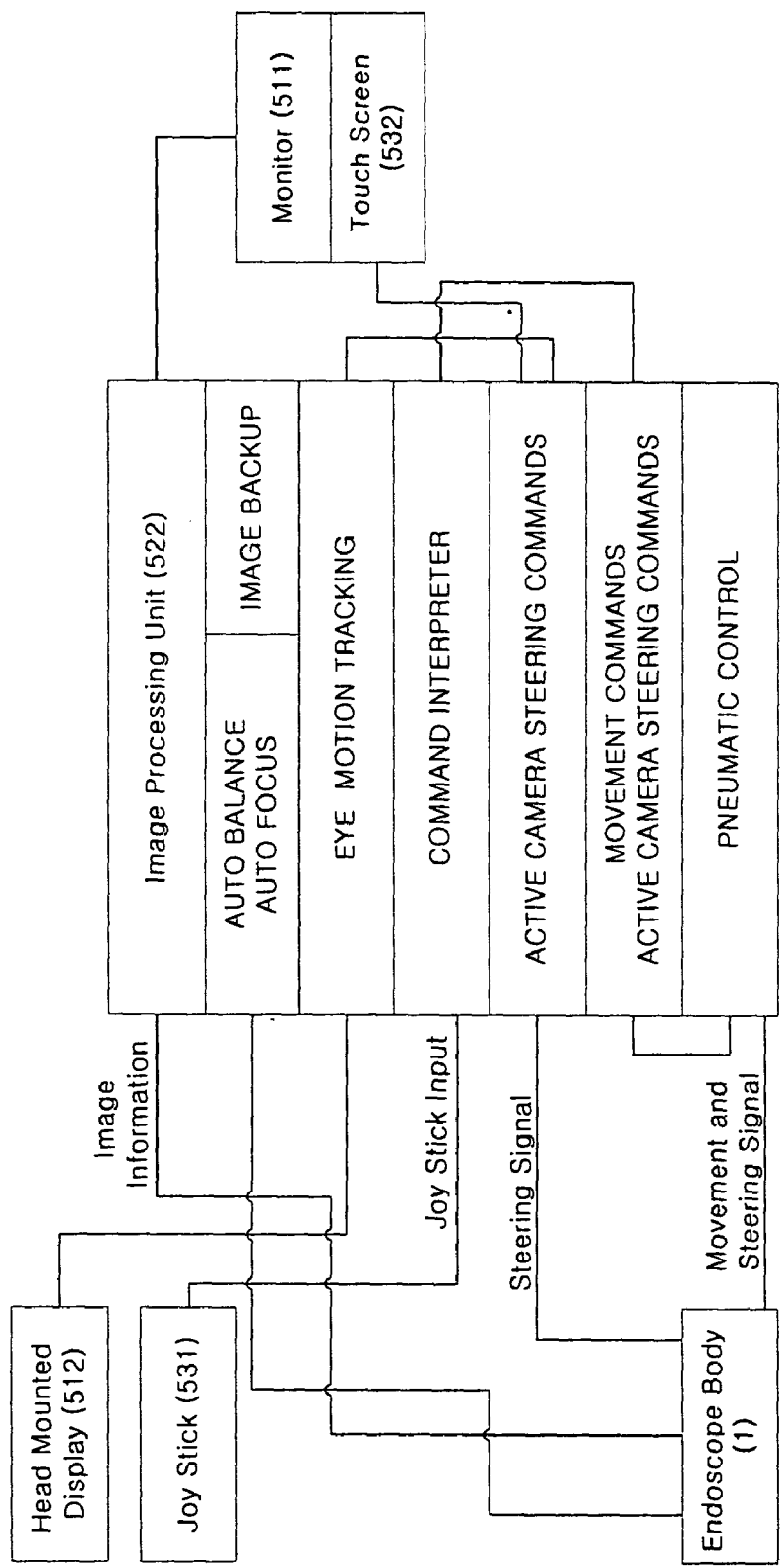
FIG. 8 is a conceptual view showing a construction relation of the endoscope system according to the present invention.

FIG. 8 is a conceptual view showing a construction relationship of the endoscope system according to the present invention.

Hereinafter, operations of the endoscope system according to the present invention will be explained in detail.

Figure 9:
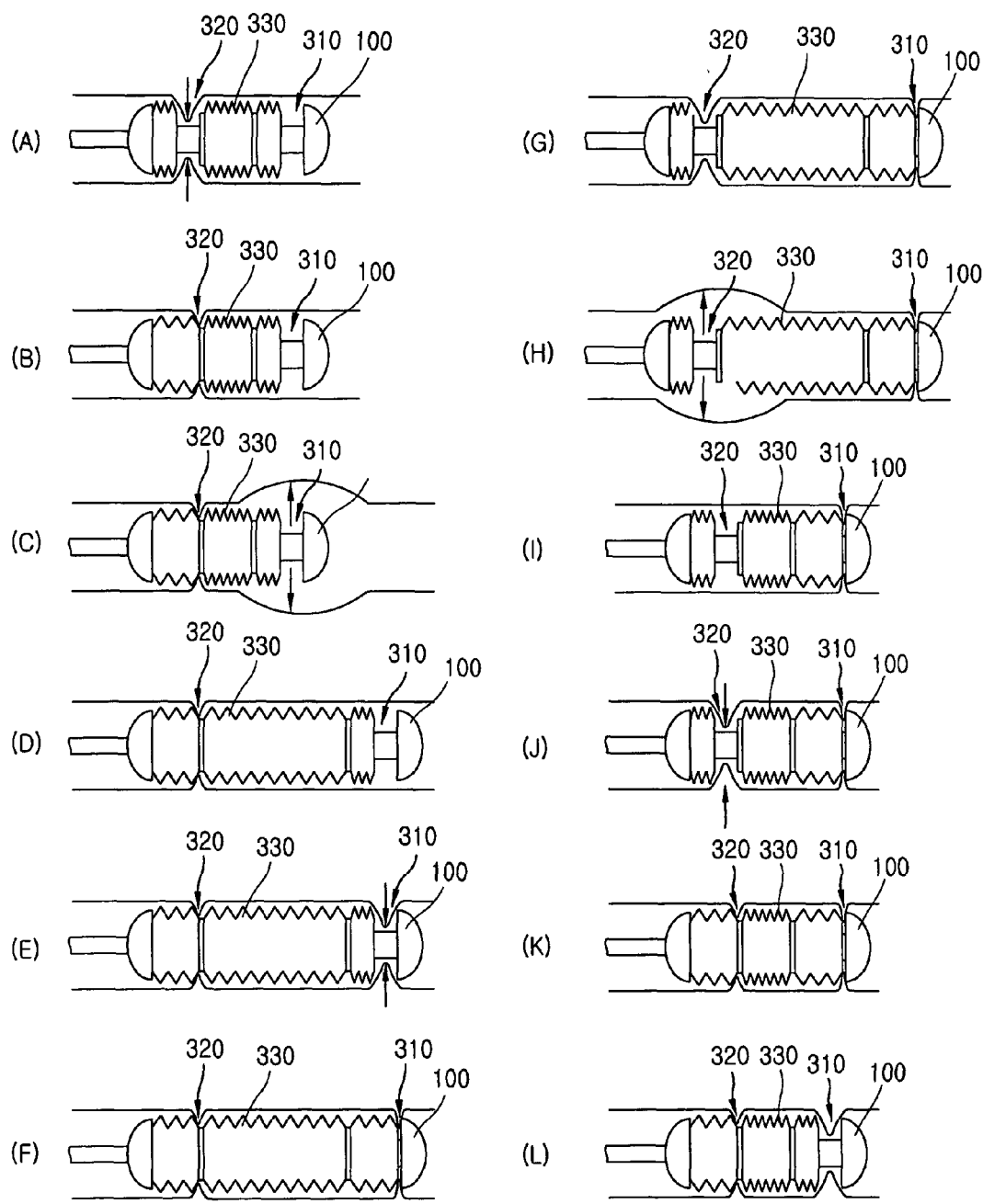
FIG. 9 is a conceptual view showing that the endoscope system according to the present invention moves.

First, as shown in FIG. 9, the body 1 of the endoscope system is inserted into the organ, especially, a large intestine L to start a movement. The body 1 forward moves by being fixed to an inner wall of the large intestine of the front fixing unit 310, releasing the fixation simultaneously with air injection of the rear fixing unit 320, contracting the moving unit 330, being fixed to the inner wall of the large intestine L of the rear fixing unit 320, releasing the fixation simultaneously with air injection of the front fixing unit 310, extending the moving unit 330, and fixing to the inner wall of the large intestine L of the front fixing unit 310. The body 1 can backward moves.

A process which the front fixing unit 310 is fixed to the inner wall of the large intestine L will be explained.

First, when air is sucked through the plurality of holes 311a formed at the outer side of the front fixing cylinder member 311a and pulled by the inner wall of the large intestine L, the front fixing bellows 314 is extended and holds the inner wall of the large intestine L. According to this, the front fixing unit 310 is fixed to the inner wall of the organ.

As the step for releasing the front fixing unit 310 from the inner wall of the large intestine L, first, air is injected through the plurality of holes 311a formed at the outer side of the front fixing cylinder member 311 and simultaneously the front fixing bellows 314 is contracted, thereby setting free the inner wall of the large intestine L. According to this, the rear fixing portion 320 is released from the inner wall of the organ.

As the step for fixing the rear fixing unit 320 to the inner wall of the large intestine L, first, when air is sucked through the plurality of holes 321a formed at the outer side of the rear fixing cylinder member 321 and thereby the inner wall of the large intestine L is pulled, the rear fixing bellows 324 is extended and holds the inner wall of the large intestine L. According to this, the rear fixing unit 320 is fixed to the inner wall of the organ As the step for releasing the rear fixing unit 320 from the inner wall of the large intestine L, first, air is injected through the plurality of holes 321a formed at the outer side of the rear fixing cylinder member 321 and simultaneously the rear fixing bellows 324 is contracted, thereby setting free the inner wall of the large intestine L. According to this, the rear fixing unit 320 is released from the inner wall of the organ.

The observer can see the inner wall of the organ through the monitor 511 or the head mounted display 512 from the obtained image by the camera 111 with the movement of the body 1. Especially, in case that the diagnosis tool is mounted to the head unit 100, a state of the large intestine L can be observed through the diagnosis tool 130.

At this time, the imaging direction of the camera 111 or the movement of the body 1 are controlled through the control unit 510 and the observer's pupil's movement is recognized by the recognizing unit 520, so that the imaging direction of the camera 111 and the movement of the body 1 are synchronized to be controlled without additional control means such as the joy stick 531 and the touch screen 532. The observer can also control through the joy stick 531 or the touch screen 532.

In the endoscope system according to the present invention, since the cylinder is formed, a space where an additional diagnosis tool or a treatment tool are mounted can be provided.

Also, in the present invention, the endoscope system having a new concept of a user interface familiar to a human can easily move and inspect in the organs, thereby enabling an intuitive fabrication. As the result, a training for fabricating the endoscope system is not required and a medical accident rarely happens. Also, a doctor can concentrate only on a determination of a sick part, thereby enhancing a fabrication of the endoscope system and a determination rate of the sick part.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. An endoscope system having a body comprising:
   a cylinder having a head unit mounted by a camera device at one side thereof and connected to a tube which is connected to an external device out of a human body at the other side thereof;
   a front fixing unit connected to the head unit, installed to an outer circumference of the cylinder, and thereby fixable to an inner wall of an organ;
   a rear fixing unit slidably installed at the outer circumference of the cylinder and fixable to the inner wall of the organ; and
   a moving unit connectedly installed between the front fixing unit and the rear fixing unit for moving the head unit in the organ by an extension and contraction when the front fixing unit or the rear fixing unit fixes the head unit to the inner wall of the organ; wherein the moving unit forming a hermetic space comprises a double moving bellows having a sectional surface of a doughnut shape, and the moving bellows is extended or contracted by an amount of inner air of the hermetic space.

2. The system of claim 1, wherein a diagnosis tool is additionally mounted to the head unit.

3. The system of claim 2, wherein the diagnosis tool is dye reacting with a cancer cell.

4. The system of claim 1, wherein the head unit is additionally provided with a frequency generating unit for generating a frequency for virtual biopsy.

5. The system of claim 1, wherein the head unit is additionally provided with a light source of infrared rays.

6. The system of claim 1, wherein the camera device additionally includes a steering system for adjusting an imaging direction of the camera device.

7. The system of claim 6, wherein the steering system includes an upper plate on which the camera device is mounted; a lower plate fixed to the head unit; and a plurality of connecting bridges for changing the imaging direction of the camera device by connecting the upper plate and the lower plate and having a changed length thereof.

8. The system of claim 7, wherein the connecting bridge is a functional polymer.

9. The system of claim 7, wherein the connecting bridge is a pneumatic cylinder.

10. The system of claim 1, further comprising:
    a recognizing unit for recognizing a movement of an observer's pupil; and a controlling unit for generating a control signal according to the pupil's movement recognized by the recognizing unit,
    wherein an image position of the camera device and a movement of the body are controlled by a signal of the control unit.

11. The system of claim 10, wherein an image outputting device for outputting an image obtained by the camera device is a head mounted display.

12. The system of claim 11, wherein the recognizing unit recognizes the pupil's movement by measuring an electromyogram of a muscle around the observer's eyes.

13. The system of claim 11, wherein the control unit adjusts a focus distance of the camera device according to a pupil's state of the recognizing unit.

14. The system of claim 11, wherein the camera device further includes an illuminating device for illuminating so that the camera device can obtain images, and the control unit controls brightness of the illuminating device according to the pupil's state of the recognizing unit.

15. The system of claim 10, wherein the recognizing unit includes:
    a recognizing camera device for imaging the observer's eyes; and
    an image processing unit for recognizing the pupil's movement from an image obtained by the recognizing camera device.

16. The system of claim 15, wherein the recognizing camera device is attached to the head mounted display.

17. The system of claim 1, further comprising a joy stick for controlling an image location of the camera device and a movement of the body.

18. The system of claim 1, further comprising a touch screen for controlling an image location of the camera device and a movement of the body.

* * * * *